United States Patent [19]
Durbin

[11] Patent Number: 4,878,508

[45] Date of Patent: Nov. 7, 1989

[54] DENTAL DEVICE FOR CLEANING TEETH

[76] Inventor: Douglas D. Durbin, 851 Corporate Dr. Ste. 201, Lexington, Ky. 40503

[21] Appl. No.: 172,775

[22] Filed: Mar. 28, 1988

[51] Int. Cl.⁴ ............................................. A61C 15/00
[52] U.S. Cl. ..................................... 132/329; 433/148; 433/149
[58] Field of Search ...................... 132/329; 128/62 A; 433/51, 148, 149

[56] References Cited

U.S. PATENT DOCUMENTS

| | | | |
|---|---|---|---|
| 1,468,125 | 0/0000 | Nielsen | 132/329 |
| 1,555,111 | 0/0000 | Flowers | 132/329 |
| 2,008,206 | 0/0000 | Grant | 132/329 |
| 3,779,256 | 12/1973 | Maloney et al. | 132/329 |
| 4,271,854 | 6/1981 | Bengtsson | 132/329 |
| 4,449,933 | 5/1984 | Forni | 433/141 |
| 4,570,653 | 0/0000 | Wolf | 132/329 |

FOREIGN PATENT DOCUMENTS

| | | | |
|---|---|---|---|
| 1084872 | of 0000 | Fed. Rep. of Germany . | |
| 2519543 | 1/1982 | France | 132/329 |

Primary Examiner—Robert Peshock
Attorney, Agent, or Firm—King & Schickli

[57] ABSTRACT

A dental device for cleaning teeth includes a resilient, elongated body member. The body member has two sides joined together so as to form a substantially V-shaped cross-section. Both inner and outer surfaces of each side include texturing in the form of cilia. In addition, spaced ridges may be provided on the sides to further aid in cleaning teeth. Each side also includes beaded edges to substantially prevent any cutting of gingival tissue when the device is used to clean between teeth. Finally, bristles may be provided along a section of the body member so that the device may be more effectively used to clean the open faces and chewing surfaces of the teeth.

11 Claims, 1 Drawing Sheet

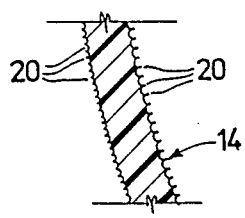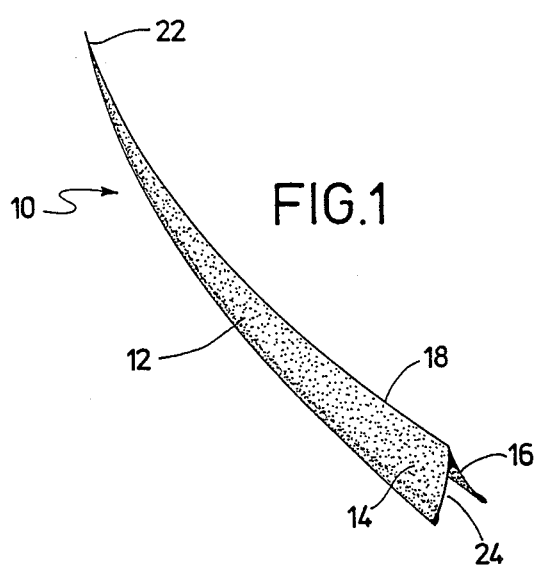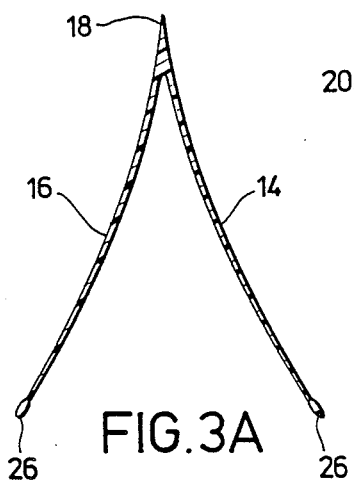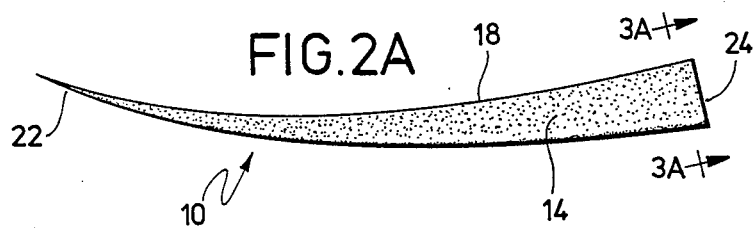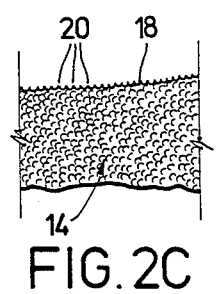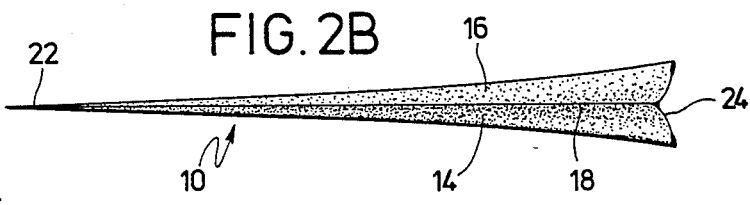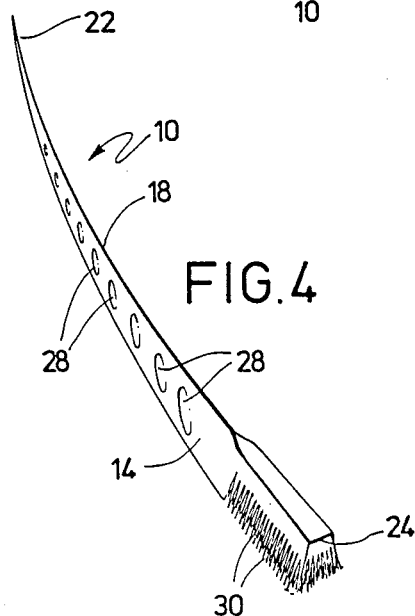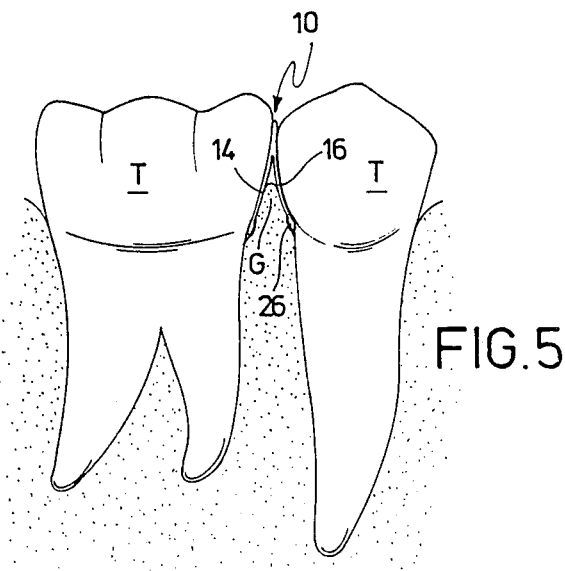

DENTAL DEVICE FOR CLEANING TEETH

TECHNICAL FIELD

The present invention relates generally to the oral hygiene field and, more specifically, to a dental device that is specially adapted for cleaning teeth, particularly, the sides of teeth even down in the pocket between the teeth and gums while protecting the gums from cutting with the device.

BACKGROUND OF THE INVENTION

Plaque is a mucous film constantly forming on teeth. It harbors bacteria and is the primary cause of tooth decay as well as periodontal or gum disease. Periodontal disease is the major cause of tooth loss in adults.

When you eat, the bacteria in plaque uses the sugar in your food and produces acid and other by-products that irritate the teeth and gums. More specifically, the acids attack the tooth enamel and break it down. To further complicate the problem the sticky plaque tends to hold the acids on the teeth prolonging the attack and further promoting decay. Meanwhile, the irritants in plaque inflame the gums making them tender and likely to bleed.

If the plaque is not removed by careful and, preferably, daily cleaning, it tends to build up. This allows the bacteria to form into colonies that are particularly harmful. Over time, cavities can form in the teeth and, the gums can become so irritated they pull away from the teeth. Thus, deep pockets are formed between the teeth and gums. These pockets become filled with bacteria and eventually pus. If the disease is not properly treated, healthy teeth eventually become loose and may in fact be lost.

A number of dental devices are known for controlling and removing plaque from teeth. The toothbrush is particularly effective in removing plaque from the exposed surfaces of the teeth including the inner and outer faces and the chewing surfaces. The bristles of a toothbrush, however, are not effective in reaching between the teeth and cleaning the plaque from the surfaces of the adjacent teeth that are in juxtaposition. Unfortunately, the space between teeth is particularly susceptible to the buildup of plaque. In order to avoid dental decay, this plaque must be removed.

Dental floss and toothpicks are known, useful devices for cleaning between teeth. Dental floss is particularly useful in cleaning the juxtaposed surfaces of adjacent teeth. The floss is wrapped around the index fingers of each hand. The floss extending between the fingers is pulled taut and carefully worked down between the teeth into the small pocket that exists between the gum papilla and the side of a tooth. The floss may then be moved up and down to clean the side of the tooth as well as lift any plaque from the pocket.

It should be recognized, however, that dental floss is only effective when properly utilized and the proper technique of use is difficult to learn. In addition, many individuals find the use of floss inconvenient, time consuming and even frustrating. Thus, it should be appreciated that for many individuals dental floss is not an effective solution to the problem of removing plaque from between teeth.

If carefully used, the pointed end of a wooden or plastic toothpick may be pushed between adjacent teeth to scrape plaque from the juxtaposed surfaces of the teeth. People who use toothpicks regularly, however, tend to damage and actually scrape away the gum papilla thereby creating an even larger space between the teeth that trap food particles and hold plaque. Preferably, this undesirable result should be avoided if at all possible.

Recognizing the shortcomings of dental floss and toothpicks in removing plaque from between teeth, some efforts have been made to design a new dental device for this purpose. Perhaps the most significant device of this type is disclosed in U.S. Pat. No. 4,570,653 to Wolf. Wolf discloses a straight piece of resilient material having a substantially V-shaped cross-section. The device may be moved back and forth between teeth while straddling the gum papilla with the smooth sides of the device extending down along the juxtaposed surfaces of the teeth.

While this device does provide for relatively effective cleaning of plaque from juxtaposed teeth surfaces while protecting the gum papilla, it is not without its disadvantages. More specifically, because the device is straight it is difficult to manipulate over the lip and across the gum of the individual whose teeth are being cleaned. The device also includes square, sharp edges on each side. These edges tend to cut into the gum when the device is pushed down into the pocket between the gum papilla and adjacent teeth to clean the sides of the teeth.. Cuts of this type are exceedingly painful and no doubt often lead an individual to stop using the device. A need is therefore identified for an improved dental device for cleaning plaque from teeth and more particularly from the juxtaposed surfaces of adjacent teeth.

SUMMARY OF THE INVENTION

Accordingly, it is a primary object of the present invention to provide a dental device for cleaning plaque from between teeth overcoming the above-described limitations and disadvantages of the prior art.

Another object of the present invention is to provide a plaque cleaning device that is both inexpensive to produce and simple to use effectively.

Still another object of the present invention is to provide a dental device particularly adapted to allow convenient and effective removal of plaque from between teeth.

Yet another object of the present invention is to provide a dental device particularly adapted for cleaning the sides of teeth even down in the pocket between the teeth and gingival tissue while protecting the gingival tissue from painful cutting with the device.

Still another object of the present invention is to provide a combined dental device for flossing and brushing wherein the device may be effectively utilized for cleaning exposed surfaces of the teeth as well as between teeth including the sides of teeth down in the pocket between the teeth and gums.

Additional objects, advantages, and other novel features of the invention will be set forth in part in the description that follows and in part will become apparent to those skilled in the art upon examination of the following or maybe learned with the practice of the invention. The objects and advantages of the invention may be realized and obtained by means of the instrumentalities and the combinations particularly pointed out in the appended claims.

To achieve the foregoing and other objects, and in accordance with the purposes of the present invention as described herein, an improved apparatus is provided for cleaning teeth. The apparatus or dental device includes a resilient, elongated body member. The flexibility of the body member allows the device to be utilized to effectively clean various tooth and gum anatomies as may be present in an individual. The body member has two sides joined together along a line so as to form a substantially V-shaped cross-section. The sides of the body member are textured to provide the most effective and efficient cleaning of the teeth. In addition, the distal edges of the sides include means for substantially preventing the cutting of gingival tissue when the device is used to clean between teeth along the gum line.

Preferably, the texturing of the sides is in the form of cilia. Thus, as the body member is manipulated back and forth and up and down across the surfaces of the teeth the cilia serve to scrub the sticky plaque away in the same manner as the bristles of a toothbrush. In order to prevent the cutting of the gingival tissue as the dental device is manipulated back and forth along the gum line, the distal edges of each side are rounded or beaded. By reducing discomfort that would be associated with this activity, this device serves to promote cleaning down along the gum line where bacteria colonies are often found and cavities tend to form.

In order to aid in the manipulation of the device, the body member includes a substantially, pointed lead end and a relatively wide, truncated tail end. Advantageously, the pointed end may be readily positioned in the gap between adjacent teeth just above the gum papilla. Further, the wide tail end allows the device to be securely gripped between the fingers of the user for better control. In order to maintain the device free from contact with the lips and gums of the user during manipulation, the body member is arcuate along the line joining the sides together. This, of course, makes it easier for the individual to move the device in the desired manner into the gap between teeth to fully clean the teeth surfaces without damaging the gums.

In order to further aid in cleaning plaque from the teeth and particularly along the juxtaposed surfaces of adjacent teeth, spaced ridges may be provided along the sides of the body member. As these ridges are moved across the teeth surfaces during insertion and removal from between teeth, they provide an added scrubbing action to remove stubborn, sticky plaque. The ridges are particularly effective for this purpose since the resilient memory of the sides tends to press the sides and the ridges against the teeth surfaces as the device is manipulated back and forth and up and down.

The dental device may also be designed to provide full purpose cleaning action for the teeth. More particularly, bristles may be provided along one section of the body member. Where the body member is formed of nylon, the bristles may be actually molded in one piece with the body member. Where the bristles are formed adjacent the tail end of the dental device, the device is turned around, held by the user at the lead end and manipulated in a circular motion across the surfaces of each tooth in the manner of a toothbrush. Thus, the device can be effectively utilized to clean plaque from the exposed surfaces of the teeth as well.

Still other objects of the present invention will become readily apparent to those skilled in this art from the following description wherein there is shown and described a preferred embodiment of this invention, simply by way of illustration of one of the modes best suited to carry out the invention. As it will be realized, the invention is capable of other different embodiments, and its several details are capable of modifications in various, obvious aspects all without departing from the invention. Accordingly, the drawing and descriptions will be regarded as illustrative in nature and not as restrictive.

BRIEF DESCRIPTION OF THE DRAWING

The accompanying drawing incorporated and forming a part of the specification, illustrates several aspects of the present invention, and together with the description serves to explain the principals of the invention. In the drawing:

FIG. 1 is a perspective view of the dental device of the present invention;

FIG. 2A is a side elevational view of the dental device;

FIG. 2B is a top plan view;

FIG. 2C is an enlarged cutaway view showing the texturing of a side of the dental device;

FIG. 3A is a tail end elevational view of the device;

FIG. 3B is an enlarged cross-sectional view through a side of the device to show the texturing in detail;

FIG. 4 is a perspective view of an alternative embodiment of the dental device including spaced ridges and a bristle section;

FIG. 5 is a schematic view showing use of the device of FIG. 1 to clean between adjacent teeth.

Reference will now be made in detail to the present preferred embodiment of the invention, an example of which is illustrated in the accompanying drawing.

DETAILED DESCRIPTION OF THE INVENTION

Reference is now made to drawing FIG. 1 showing the dental device 10 of the present invention for cleaning teeth. The dental device 10 includes a resilient, elongated body member 12. The body member 12 includes two sides 14, 16 joined together along line 18 at an angle of substantially 45 degrees to form a substantially V-shaped cross-section. Preferably, the body member is formed from a nylon material to provide the necessary resiliency. In addition, the material includes micro-filaments so as to provide a textured surface along both faces of each side similar to cilia 20 (see FIGS. 2C and 3B).

In order to allow easier manipulation of the dental device 10 when cleaning between teeth as shown in FIG. 5, the device 10 includes a substantially pointed lead end 22 and a relatively wide, truncated tail end 24. Advantageously, the pointed lead end 22 allows the user to access the device into very small or narrow areas as, for example, may be present between adjacent teeth. Conversely, the relatively wide, truncated tail end 24 is easily and securely held between the fingers of the user to allow excellent control during manipulation.

In addition, as best shown in FIG. 2A, the device is arcuate. More specifically, the device is gently curved about a radius of approximately 4 to 6 inches along line 18 in a direction away from the sides 14, 16. This allows the user of the device 10 to more easily place the device between teeth in an effort to clean that area even down along the gum line. Further, the upwardly directed curvature allows the lead end 22 of the device to emerge from between teeth on the lingual or palatal side without damaging the gum tissue.

In order to further prevent the device 10 from cutting the gingival tissue or gum G when used to clean between teeth as shown in FIG. 5, the distal edges 26 of the sides 14 and 16 are beaded (see figure 3A). The beading or rounding of the edges 26 assures that there are no sharp corners at the ends of the sides to cut into the soft gingival tissue. This has been a major problem with prior art devices that has resulted in the failure of those devices to be successfully positioned in the marketplace. After suffering painful gum cutting with prior art toothpick devices designed to clean between teeth, individuals have chosen to return to the use of dental floss or simply not clean between teeth between dental appointments. Since many individuals do not properly use dental floss this problem has effectively caused these individuals to suffer from inadequate dental care.

An alternative embodiment of the dental device 10 of the present invention is shown in figure 4. The alternative embodiment also includes a resilient elongated body member 12 having two sides joined together along line 18 so as to form a substantially V-shaped cross-section. Each of the sides 14, 16 may include spaced ridges 28 to provide additional cleaning action when the device is moved back and forth between teeth. Further, one section of the device, such as the tail end 24, may include a group of bristles 30. These bristles may be molded directly with the nylon body member 12.

Advantageously, the bristles 30 may be used in the same manner as a toothbrush to clean the exposed surfaces of the teeth including the inner and outer faces as well as the chewing surfaces. Thus, the device of the present invention may act as a combined flossing and brushing device that may be used to effectively clean each entire tooth, including the sides of the teeth even in the pocket between each tooth and the surrounding gingival tissue. Because the device 10 is small and molded from lightweight nylon it is particularly convenient for use by an individual when traveling. In addition, the device 10 is inexpensive to produce and effectively disposable. Thus, it could be provided by airlines with meals and in individual bathrooms in hotel rooms or any other appropriate setting for convenient dental care.

The proper use of the dental device 10 to clean between teeth is best shown in FIG. 5. The user first inserts the lead end 22 of the device between the teeth T to be cleaned. Once the device is inserted the user moves the device back and forth between the teeth while carefully drawing the device down along the sides of the teeth. This manipulation continues until the sides 14, 16 extend down into the pocket formed between the gingival tissue or gum papilla G and the juxtaposed sides of the teeth T. During this manipulation, the outer surfaces of the sides 14, 16 are biased by the resilient material to bring the cilia 20 into scraping engagement with the teeth so as to scrub sticky plaque from the teeth. If the device 10 includes ridges 28, these ridges provide even more concentrated scraping action for more effective cleaning of plaque and also tartar. In addition, the flexible sides 14, 16 even allow "compression" curvature so as to accomodate convex dental surfaces of teeth and maintain the sides in cleaning contact.

Once the device 10 is positioned with the side edges 26 extending down into the pockets between the teeth T and gum papilla G, the device may continue to be moved back and forth and up and down. The cilia 20 on the outer surfaces of the sides 14, 16 and the ridges 28 provide excellent cleaning action to the sides of the teeth in the pockets even down below the gum line where cavities might otherwise form. In addition, the cilia 20 on the inner surface of each side 14, 16 serves to gently massage the gum papila while also providing additional cleaning action serving to remove trapped food and plaque from the pocket. It should be appreciated, however, that the open channel formed between the sides 14, 16 prevents damaging contact with the gum papilla G. Further, the beaded edges 26 aid in preventing the device 10 from cutting into the soft gingival tissue or gums G as the device is moved back and forth.

In summary, numerous benefits result from employing the concepts of the present invention. The dental device 10 of the present invention provides very efficient and effective cleaning of the teeth. More specifically, the resilient memory of the device serves to press the sides 14, 16 against the sides of the teeth being cleaned. The texturing or cilia 20 and/or spaced ridges 28 provide extremely effective cleaning action to remove plaque and even tartar build-up from the surfaces of the teeth. In addition, the arcuate shape of the dental device 10 along the line 18 joining the sides 14, 16 serves to allow the user to easily and properly position the device between the teeth for cleaning. Advantageously, the beaded distal edges 26 of each side 14, 16 provide smooth rounded surfaces that resist or substantially prevent cutting of the soft gingival tissue as the device is moved back and forth when cleaning along the gum line.

The foregoing description of a preferred and alternative embodiment of the invention has been presented for purposes of illustration and description. It is not intended to be exhaustive or to limit the invention to precise forms disclosed. Obvious modifications or variations are possible in light of the above teachings. The embodiments were chosen and described to provide the best illustration and the principles of the invention and its practical application to thereby enable one of ordinary skill in the art to utilize the invention in a various embodiments and with various modifications as are suited to the particular use contemplated. All such modifications and variations are within the scope of the invention as determined by the appended claims when interpreted in accordance with the breadth to which they are fairly, legally and equitably entitled.

I claim:

1. A dental device for cleaning teeth, comprising:
a resilient, elongated body member having two sides joined together along a line to form a substantially V-shaped cross-section, said body member further including texture means in the form of cilia on said sides for cleaning said teeth and means on distal edges of said sides for substantially preventing cutting of gingival tissue when said dental device is used to clean between teeth.

2. The dental device set forth in claim 1, wherein said means for preventing cutting of gingival tissue is a beaded edge on each of said sides.

3. The dental device set forth in claim 1, wherein said body member is arcuate about a radius of substantially 4 to 6 inches along said line joining said sides together.

4. The dental device set forth in claim 1, wherein said body member includes a substantially pointed, lead end and a relatively wide, truncated tail end.

5. The dental device set forth in claim 1, wherein said body member includes spaced ridges along said sides to further aid in cleaning said teeth.

6. The dental device set forth in claim 1, wherein bristle means are provided on one section of said body member to further aid in cleaning said teeth.

7. The dental device set forth in claim 2, wherein said cilia is provided on opposing faces of each side.

8. A dental device for cleaning teeth, comprising:
a resilient, elongated body member having two sides joined together to form a substantially V-shaped cross-section; said body member further including texture means on said sides and bristle means on one section of said body member for cleaning said teeth as well as means on distal edges of said sides for substantially preventing cutting of gingival tissue when said dental device is used to clean between teeth.

9. The dental device set forth in claim 8, wherein said means for preventing cutting gingival tissue is a beaded edge on each of said sides.

10. The dental device set forth in claim 8, wherein said body member is arcuate about a radius of substantially 4 to 6 inches along said line joining said sides together.

11. The dental device set forth in claim 8, wherein said body member includes a substantially pointed, lead end and a relatively wide, truncated tail end.

* * * * *